United States Patent
Ekser et al.

(10) Patent No.: US 12,207,629 B2
(45) Date of Patent: Jan. 28, 2025

(54) IDENTIFICATION OF PORCINE XENOANTIGENS

(71) Applicant: Indiana University Research and Technology Corporation, Indianapolis, IN (US)

(72) Inventors: Burcin Ekser, Indianapolis, IN (US); Ping Li, Carmel, IN (US)

(73) Assignee: Indiana University Research and Technology Corporation, Bloomington, IN (US)

( * ) Notice: Subject to any disclaimer, the term of this patent is extended or adjusted under 35 U.S.C. 154(b) by 373 days.

(21) Appl. No.: 17/684,207

(22) Filed: Mar. 1, 2022

(65) Prior Publication Data

US 2022/0183262 A1 Jun. 16, 2022

Related U.S. Application Data

(62) Division of application No. 16/261,065, filed on Jan. 29, 2019, now abandoned.

(60) Provisional application No. 62/623,571, filed on Jan. 30, 2018.

(51) Int. Cl.
| | |
|---|---|
| *C12N 5/071* | (2010.01) |
| *A01K 67/0278* | (2024.01) |
| *A61K 35/12* | (2015.01) |
| *A61P 43/00* | (2006.01) |
| *C12N 9/10* | (2006.01) |
| *C12N 15/90* | (2006.01) |

(52) U.S. Cl.
CPC .......... *A01K 67/0278* (2013.01); *A61K 35/12* (2013.01); *A61P 43/00* (2018.01); *A01K 2207/15* (2013.01); *A01K 2217/15* (2013.01); *A01K 2227/108* (2013.01); *A01K 2267/025* (2013.01); *C12N 5/0602* (2013.01); *C12N 9/1051* (2013.01); *C12N 15/907* (2013.01)

(58) Field of Classification Search
CPC .. C12N 5/0602; C12N 9/1051; C12N 15/907; C12N 2510/00; A01K 67/0276; A01K 2217/075; A01K 2267/025
See application file for complete search history.

(56) References Cited

U.S. PATENT DOCUMENTS

| | | |
|---|---|---|
| 7,989,675 B2 | 8/2011 | Welsh et al. |
| 2003/0190663 A1 | 10/2003 | Yang et al. |
| 2009/0241203 A1 | 9/2009 | Welsh et al. |
| 2014/0017215 A1 | 1/2014 | Ayares |
| 2017/0311579 A1 | 11/2017 | Tector, III |

FOREIGN PATENT DOCUMENTS

WO 2016210280 A1 12/2016

OTHER PUBLICATIONS

Li et al., Sep. 20, 2017 (Xenotransplantation, vol. 24, No. 5, Abstract No. O.3.6).*
International Searching Authority, International Search Report and Written Opinion for application PCT/US2018/015644, mailed on Jun. 6, 2019.
Ekser, et al., Clinical Xenotransplantation: The Next Medical Revolution?, Lancet, 2012, 379(9816):672-683.
Hemler, Tetraspanin Proteins Mediate Cellular Penetration, Invasion, and Fusion Events and Define a Novel Type of Membrane Microdomain, Annu. Rev. Cell Dev. Biol., 2003, 19:397-422.
Hemler, Tetraspanin Functions and Associated Microdomains, Nature Reviews Molecular Cell Biology, 2005, 6:801-811.
Jones, et al., Tetraspanins in Cellular Immunity, Biochemical Society Transactions, 2011, 39:506-511.
Maecker, et al., CD81 on B Cells Promotes Interleukin 4 Secretion and Antibody Production During T Helper Type 2 Immune Responses, Proc. Natl. Acad. Sci. USA, 1998, 95:2458-2462.
Ostedgaard, et al., The ΔF508 Mutation Causes CFTR Misprocessing and Cystic Fibrosis-Like Disease in Pigs, Science Translational Medicine, 2011, 3(74):74ra24.
Robak, et al., Anti-CD37 Antibodies for Chronic Lymphocytic Leukemia, Expert Opinion on Biological Therapy, 2014, 14(5):651-661.
Rogers, et al., Disruption of the CFTR Gene Produces a Model of Cystic Fibrosis in Newborn Pigs, Science, 2008, 321(5897):1837-1841.
Rogers, et al., Production of CFTR-null and CFTR-AF508 Heterozygous Pigs by Adeno-Associated Virus-Mediated Gene Targeting and Somatic Cell Nuclear Transfer, Journal of Clinical Investigation, 2008, 118(4):1571-1577.
Vajta, et al., Somatic Cell Cloning Without Micromanipulators, Cloning, 2001, 3(2):89-95.
Vajta, Handmade Cloning: The Future Way of Nuclear Transfer?, Trends in Biotechnology, 2007, 25(6):250-253.
Van Spriel, Tetraspanins in the Humoral Immune Response, Biochemical Society Transactions, 2011, 39:512-517.
Saleh et al., Identification of the Tetraspanin CD82 as a New Barrier to Xenotransplantation, Journal of Immunology, 2013, 191:2796-2805.
European Patent Office, Extended Search Report, Application No. 19747686.4, Sep. 20, 2021, 7 pages.

(Continued)

*Primary Examiner* — Shin Lin Chen
(74) *Attorney, Agent, or Firm* — Quarles & Brady, LLP (57) ABSTRACT

Provided herein are genetically modified pigs, porcine organs, tissue, and cells having a reduced propensity to cause a rejection response in a human subject following xenotransplantation. In particular, provided herein are genetically modified pigs lacking nonGal xenoantigens, and porcine cells, tissues, and organs obtained from such genetically modified pigs that are suitable for transplantation into a human. Also provided herein are methods of improving a rejection related symptom in a human subject.

5 Claims, 10 Drawing Sheets

Specification includes a Sequence Listing.

(56) References Cited

OTHER PUBLICATIONS

Wang, Y., Du, Y., Shen, B., Zhou, X., Li, J., Liu, Y., . . . & Wei, H. (2015). Efficient generation of gene-modified pigs via injection of zygote with Cas9/sgRNA. Scientific reports, 5(1), 1-9.
Wang, K., Ouyang, H., Xie, Z., Yao, C., Guo, N., Li, M., . . . & Pang, D. (2015). Efficient generation of myostatin mutations in pigs using the CRISPR/Cas9 system. Scientific reports, 5(1), 1-11.
Khodarovich et al., 2013, Applied Biochemistry and Microbiology, vol. 49, No. 9, pp. 711-722.
Selsby et al., 2015, ILARJournal, vol. 56, No. 1, p. 116-126.
Maksimenko et al., 2013, Acta Naturae, vol. 5, No. 1, p. 33-46.
Yang et al., 2016, PNAS, 113(41), E6209-E6218, p. 1-10.
Guo et al., 2015, Cell Research, vol. 25, p. 767-768.
Kang et al., 2018, Human Molecular Genetics, vol. 27, No. 2, p. 211-223.
Adams, A. B. et al. Xenoantigen Deletion and Chemical Immunosuppression Can Prolong Renal Xenograft Survival. Ann Surg 268, 564-573, doi:10.1097/SLA.0000000000002977 (2018).
Alter, G., Malenfant, J. M. & Altfeld, M. CD107a as a functional marker for the identification of natural killer cell activity. J Immunol Methods 294, 15-22, doi:10.1016/j.jim.2004.08.008 (2004).
Cooper, D. K. C. et al. Justification of specific genetic modifications in pigs for clinical organ xenotransplantation. Xenotransplantation 26, e12516, doi:10.1111/xen.12516 (2019).
Cooper, D. K., Ekser, B., Ramsoondar, J., Phelps, C. & Ayares, D. The role of genetically engineered pigs in xenotransplantation research. J Pathol 238, 288-299, doi:10.1002/path.4635 (2016).
Estrada, J. L. et al. Evaluation of human and non-human primate antibody binding to pig cells lacking GGTA1/CMAH/beta4GaINT2 genes. Xenotransplantation 22, 194-202, doi:10.1111/xen.12161 (2015).
Gao, H. et al. Human IL-6, IL-17, IL-1beta, and TNF-alpha differently regulate the expression of pro-inflammatory related genes, tissue factor, and swine leukocyte antigen class I in porcine aortic endothelial cells. Xenotransplantation 24, doi:10.1111/xen.12291 (2017).
Inverardi, L. et al. Early recognition of a discordant xenogeneic organ by human circulating lymphocytes. J Immunol 149, 1416-1423 (1992).
Khalfoun, B. et al. Development of an ex vivo model of pig kidney perfused with human lymphocytes. Analysis of xenogeneic cellular reactions. Surgery 128, 447-457, doi:10.1067/msy.2000. 107063 (2000).
Kwiatkowski, P. et al. Induction of swine major histocompatibility complex class I molecules on porcine endothelium by tumor necrosis factor-alpha reduces lysis by human natural killer cells. Transplantation 67, 211-218, doi:10.1097/00007890-199901270-00005 (1999).
Li et al. "Biallelic knockout of the α-1,3 galactosyltransferase gene in porcine liver-derived cells using zinc finger nucleases" J Surg Res. May 1, 2013;181(1):e39-45.
Li, P., et al. Efficient generation of genetically distinct pigs in a single pregnancy using multiplexed single-guide RNA and carbohydrate selection. Xenotransplantation 22, 20-31, doi:10.1111/xen.12131 (2015).
Lutz, A. J. et al. Double knockout pigs deficient in N-glycolylneuraminic acid and galactose alpha-1,3-galactose reduce the humoral barrier to xenotransplantation. Xenotransplantation 20, 27-35, doi:10.1111/xen.12019 (2013).
Varki, A. Diversity in the sialic acids. Glycobiology 2, 25-40, doi:10.1093/glycob/2.1.25 (1992).
Li, P., et al. Identification of novel xenoreactive non-gal antigens: tetraspanin CD37 and CD81, Xenotransplantation, Sep. 2017, vol. 24(5), 0.3.6, pp. 27-28.
Heider, KH, et al. A novel Fc-engineered monoclonal antibody to CD37 with enhanced ADCC and high proapoptotic activity for treatment of B-cell malignancies, Blood, 2011; 118 (15): 4159-4168.
Li, P., et al. Isolation, characterization, and nuclear reprogramming of cell lines derived from porcine adult liver and fat. Cell Reprogram, 2010, 12, 599-607, doi:10.1089/cell.2010.0006.
Ekser, B., Li, P. & Cooper, D. K. C. Xenotransplantation: past, present, and future. Curr Opin Organ Transplant, 2017, 22, 513-521, doi:10.1097/MOT.0000000000000463.
Lee et al. Developing genetically engineered mouse models using engineered nucleases: Current status, challenges, and the way forward, Drug Discovery Today: Disease Models, 2016, vol. 20, p. 13-20.
Tran, P. D. et al. Porcine cells express more than one functional ligand for the human lymphocyte activating receptor NKG2D. Xenotransplantation 15, 321-332, doi:10.1111/j.1399-3089.2008.00489.x (2008).
Diaz Varela, I., et al. Cross-reactivity between swine leukocyte antigen and human anti-HLA- specific antibodies in sensitized patients awaiting renal transplantation. J Am Soc Nephrol 14, 2677-2683, doi:10.1097/01.asn.0000088723.07259.cf (2003).

* cited by examiner

Cloning of pCD37 X5 isoform

Extract RNA (spleen) → RT-PCR

Ta-1  Ta-2

642 bp →

ATGGGGCCTTGCCCTCCTGGGGTGTGTGGGGCCCTGAAGGAGTTCCGCTGCTGGCCTGTATTTTGGGGACT
GCTGCTCCTGTTTGCCACGCAGATCACCCTGGGAATCCTCCACGCAGCCAGTCAGTCCGGAAAGTGA
AGGACATCGTGCTGAAGACATACCGCGTCCAGAACTACCGGCCGGAGAGGACACGCGGCCGGAGAGAGTTGGGACT
ACGTGCAGTTCAGCTGCGCTGCAGTTCCTGGAACTCTCGTATCCCACCGGAGGAGCAAC
GAGTCGGAGTGCACCTGTCGCCCTGCTCCTGCTATAACTCATCCGCGACCAGTCCGAATCTGAATCTTCGATACGTTC
TACTTGTCCCAGTTCAGCCGACCCAGAGGCGACACAGGCGACACATTTGCCCTGGTCCTGCAAA
CAGCCACATCTACAGAGAGGGCTGCGAGGGGAGCCTCAACAACTGTTGCACAACAACCTATCTCTATAGTGGGC
ATTTGTCTCGGGTCGGTCGGTCGGTCTACTCGAGCTTCATGACGCTGTCCATGTCCATGTCCATGTCCATGTCC
TACGACCGGCTTGCTGGTACCGCTAG (SEQ ID NO:4)

FIG. 9

Crispr/Cas9 induced mutation in pCD37 gene

CACCATGGGCCTTGCCCTCCTGG (WT)
CACCATGGGCCTTGCCCNNNNN

FIG. 10

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence

```
<220> FEATURE:
<223> OTHER INFORMATION: X5 forward primer

<400> SEQUENCE: 1
atgggccttg ccctcctgg                                                        19

<210> SEQ ID NO 2
<211> LENGTH: 18
<212> TYPE: DNA
<213> ORGANISM: Artificial Sequence
<220> FEATURE:
<223> OTHER INFORMATION: Reverse X5 primer

<400> SEQUENCE: 2
ctagcggtac cgagcccg                                                         18

<210> SEQ ID NO 3
<211> LENGTH: 18
<212> TYPE: DNA
<213> ORGANISM: Artificial Sequence
<220> FEATURE:
<223> OTHER INFORMATION: Forward X2 primer

<400> SEQUENCE: 3
atgtcggccc aggccagc                                                         18

<210> SEQ ID NO 4
<211> LENGTH: 642
<212> TYPE: DNA
<213> ORGANISM: Sus domesticus

<400> SEQUENCE: 4
atgggccttg ccctcctggg ctgtgtgggg gccctgaagg agttccgctg cctgctgggc            60
ctgtattttg gggcactgct gctcctgttt gccacgcaga tcaccctggg aatcctcatc           120
tccacgcagc gagtccagct ggtgcggaaa gtgaaggaca tcgtgctgaa gaccatccag           180
aactaccgcg tccacccaga ggagacagcg gccgaggaga gttgggacta cgtgcagttt           240
cagctgcgct gctgcggctg gaactctcct cgggattggt tccgtatccc caccctgagg           300
agcaacgagt cggacgtgca cctcgtgccc tgctcctgct ataactcatc cgcgaccaac           360
gactctgcaa tcttcgatac gttctacttg tcccagttca gccggcccag accacaggcg           420
cagtccggac acaatgcaga catttgcgtg gtccctgcaa acagccacat ctacagagag           480
ggctgcgagg ggagcctcaa caactggttg cacaacaacc tcatctctat agtgggcatt           540
tgtctcggcg tcggtctact cgagctcagc ttcatgacgc tgtccatgtt cctgtgcaga           600
aacctggacc atgtctacga ccggcttgct cggtaccgct ag                             642
```

IDENTIFICATION OF PORCINE XENOANTIGENS

CROSS-REFERENCE TO RELATED APPLICATIONS

This application is a divisional of U.S. application Ser. No. 16/261,065, filed Jan. 29, 2019, which claims priority to U.S. Provisional Patent Application No. 62/623,571, filed on Jan. 30, 201. Each of the above-referenced applications is incorporated by reference in its entirety as if fully set forth herein.

SEQUENCE LISTING

A Sequence Listing accompanies this application and is submitted as an ASCII text file of the sequence listing named "144578_00275_ST25.txt" which is 1728 bytes in size and was created on Mar. 1, 2022. The sequence listing is electronically submitted via EFS-Web with the application and is incorporated herein by reference in its entirety.

BACKGROUND

Pigs genetically modified (i.e., transgenic, genetically engineered) to remove major xenoreactive antigens ("xenoantigens"), such as a triple knock-out that removes αGal, N-glycolylneuraminic acid (NeuGc, also known as Hanganutziu-Deicher antigen), and the B4GalNT2-related glycan, have been generated. However, unknown xenoantigens remain, meaning that xenotransplanted organs from such genetically modified pigs could induce rejection (e.g., acute or acute humoral rejection) in the recipient. Accordingly, there remains a need in the art for genetically modified porcine cells and tissues lacking xenoreactive antigens that present a critical barrier to clinical xenotransplantation.

SUMMARY OF THE DISCLOSURE

In a first aspect, provided herein is a transgenic pig whose genome comprises genetic modifications that result in one or more of a disrupted porcine CD37 (pCD37) gene and a disrupted porcine CD81 (pCD81) gene. Resulting from said genetic modifications, no detectable level of one or both of pCD37 and pCD81 protein is present in the transgenic pig as compared to a wild-type pig. When tissue from said transgenic pig is transplanted into a human, a rejection related symptom is improved as compared to when tissue from a wild-type pig is transplanted into a human. In some cases, the genome of the transgenic pig further comprises genetic modifications that result in lack of any expression of functional α(1,3)-galactosyltransferase (αGT), cytidine monophosphate-N-acetylneuraminic acid hydroxylase (CMAH), and β1,4 N-acetylgalactosaminyl transferase (B4GalNT2) relative to a porcine cell lacking said modifications to the genome, the transgenic pig exhibiting reduced levels of αGal antigen, Neu5GC antigen, and B4GalNT2 antigens as compared to a pig lacking said genetic modifications. Cells of the transgenic pig can exhibit reduced binding to human immunoglobulins as compared to cells from a wild-type pig.

In another aspect, provided herein are porcine organs, tissues, or cells obtained from a transgenic pig described herein. The porcine organ, tissue, or cell can be selected from skin, heart, liver, kidneys, lung, pancreas, thyroid, and small bowel, or portions thereof.

In a further aspect, provided herein is a genetically modified porcine cell comprising modifications to the genome of the porcine cell that result in one or more of (i) the lack of any expression of functional pCD37 (pCD37KO) and (ii) the lack of any expression of functional pCD81 (pCD81KO), where said genetically modified porcine cell exhibits reduced binding to human immunoglobulins relative to a porcine cell lacking said genetic modifications. The genetically modified porcine cell can further comprise modifications to the genome of the porcine cell that result in lack of any expression of functional α(1,3)-galactosyltransferase (αGT), cytidine monophosphate-N-acetylneuraminic acid hydroxylase (CMAH), and β1,4 N-acetylgalactosaminyl transferase (B4GalNT2) relative to a porcine cell lacking said modifications to the genome, where the modified porcine cell exhibits a reduced level of αGal antigens, a reduced level of Neu5GC antigens, and a reduced level of B4GalNT2 antigens as compared to a porcine cells lacking said genetic modifications.

In another aspect, provided herein is a transgenic pig derived from the genetically modified cell. In addition, provided herein is a porcine organ, tissue, or cell obtained from the genetically modified pig. The porcine organ, tissue or cell can be selected from skin, heart, liver, kidneys, lung, pancreas, thyroid, small bowel, and portions thereof.

In a further aspect, provided herein is a method of improving a rejection related symptom in a human subject comprising transplanting porcine transplant material having reduced levels of pCD37 antigens and reduced levels of pCD81 antigens into a human subject in need of a transplant, where a rejection related symptom is improved as compared to when porcine transplant material from a wild-type pig is transplanted into a human subject. The rejection related symptom can be selected from a cellular rejection response related symptom, a humoral rejection response related symptom, a hyperacute rejection related symptom, an acute humoral xenograft reaction rejection related symptom, and an acute vascular rejection response related symptom.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, where.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The genetically modified animals, organs, tissues, and cells provided herein are based at least in part on the inventor's identification and characterization of new porcine tetraspanins as nonGal xenoreactive antigens. Tetraspanin proteins play important roles in cellular and humoral immune responses, interacting with key leukocyte receptors, including MHC (major histocompatibility complex) molecules, integrins, CD4/CD8 T cells, and the B-cell receptor complex. Among the advantages of the genetically modified animals described herein, and porcine organs, tissues, and cells thereof, transgenic animals comprising genetic modifications to knock out one or both of the newly identified porcine tetraspanins present fewer xenoreactive antigens likely to induce hyperacute rejection (HAR) and other xenotransplant rejection issues in pig-to-human transplants. Accordingly, the transgenic pigs hold great promise as a solution to the shortage of organs from donor animals for xenotransplantation. In addition, the genetically modified pigs described herein are suitable for clinical trials and provide an animal model for studying the role of nonGal xenoreactive antigens in immune responses and coagulation responses to pig-to-human xenotransplantation.

Accordingly, in a first aspect, provided herein is a genetically modified porcine cell, where the genetic modifications comprise modifications to the genome of a porcine cell that result in one or more of (i) the lack of any expression of functional pCD37 (pCD37KO) and (ii) the lack of any expression of functional pCD81 (pCD81KO), where said genetically modified porcine cell exhibits reduced binding to human immunoglobulins relative to a porcine cell lacking said genetic modifications.

In certain embodiments, porcine cells genetically modified to lack expression of functional pCD37 and/or pCD81 are further genetically modified to lack expression of other xenoreactive antigens. For example, it will be advantageous in some cases to generate a triple, quadruple, or quintuple knockout transgenic pig in which its genome has been genetically modified to mutate or knock out the genes encoding pCD37 and pCD81 (e.g., pCD37/pCD81 double knock-out) plus one or more of the genes encoding α-1,3-galactosyltransferase-1 (GGTA1), Cytidine monophosphate-N-acetylneuraminic acid hydroxylase (CMAH), and β1,4-N-acetylgalactosaminyltransferase (β4GalNT2). The enzyme α-1,3-galactosyltransferase-1 (GGTA1) is required for synthesis of αGal antigen, and the enzyme CMAH is required for synthesis of N-Glycolylneuraminic acid (Neu5Gc), a sialic acid molecule found in most non-human mammals. Humans cannot synthesize Neu5Gc because the human gene CMAH is irreversibly mutated and, thus, non-functional. When further genetically modified to comprise knockouts of GGTA1, CMAH, and β4GalNT2, the genetically modified porcine cell exhibits a reduced level of αGal antigens, a reduced level of Neu5GC antigens, and a reduced level of B4GalNT2 antigens as compared to a porcine cell lacking said genetic modifications. In some cases, genetic modifications that knock out one or both of pCD37 and pCD81 are made in cells of triple-gene knockout (KO) pigs (Gal-KO/CMAH-KO/B4GalNT2-KO), which lack the major xenoantigens αGal, Neu5Gc, and B4GalNT2-related glycan.

As used herein, the term "genetic modification" and its grammatical equivalents can refer to one or more alterations of a nucleic acid, e.g., the nucleic acid within the genome of an organism or cells thereof. For example, genetic modification can refer to alterations, additions, and/or deletion of genes. A genetically modified cell can also refer to a cell with an added, deleted and/or altered gene. In some cases, cells isolated from a wild-type (not genetically modified) non-human animal such as a pig or another mammal are genetically modified for use according to a method provided herein. In some cases, the genetically modified cell is a cell isolated from a genetically modified non-human animal (e.g., a genetically modified pig). A genetically modified cell from a genetically modified non-human animal can be a cell isolated from such genetically modified non-human animal. In some cases, a genetically modified cell of a non-human animal can comprise reduced expression of one or more genes as compared to a non-genetically modified counterpart animal. A non-genetically modified counterpart animal can be an animal substantially identical to the genetically modified animal but without genetic modification in the genome. For example, a non-genetically modified counterpart animal can be a wild-type animal of the same species as the genetically modified animal.

In another aspect, transgenic non-human mammals suitable for use in xenotransplantation and methods of producing transgenic non-human mammals suitable for use in xenotransplantation are provided. In particular, the present application describes the production of homozygous single and double transgenic mammals. As used herein, the term "transgenic" refers to a non-human mammal wherein a given gene has been altered, removed or disrupted.

In certain embodiments, the transgenic animal is a pig having decreased expression of one or more nonGal xenoreactive antigens porcine CD37 and porcine CD81. Also provided herein are transgenic animals further comprising disrupted expression of one or more other xenoreactive antigens or immune-related proteins and/or overexpression of human genes. For example, transgenic pigs lacking α1,3-galactosyltransferase (αGT), which synthesizes the epitope Galα1-3Galβ1-4GlcNAc-R (αGal), can be used as a background strain for further genetic modifications. In other cases, genetic modifications are made in the triple knockout GalKO/CMAH-KO/B4GalNT2-KO background.

As used herein, the term "knockout" refers to a transgenic non-human mammal wherein a given gene has been altered, removed or disrupted. The term is intended to encompass all progeny generations. Thus, the founder animal and all F1, F2, F3 and so on progeny thereof are included, regardless of whether progeny were generated by gene editing or somatic cell nuclear transfer (SCNT) from the founder animal or a progeny animal or by traditional reproductive methods. By "single knockout" is meant a transgenic mammal wherein one gene has been altered, removed or disrupted. By "double knockout" is meant a transgenic mammal wherein two genes have been altered, removed or disrupted. By "triple knockout" is meant a transgenic mammal wherein three genes have been altered, removed or disrupted. By "quadruple knockout" is meant a transgenic mammal wherein four genes have been altered, removed or disrupted. By "quintuple knockout" is meant a transgenic mammal wherein five genes have been altered, removed, or disrupted.

The transgenic mammal may have one or both copies of the gene sequence of interest disrupted. In the case where only one copy or allele of the nucleic acid sequence of interest is disrupted, the transgenic animal is termed a "heterozygous transgenic animal." The term "null" mutation encompasses both instances in which the two copies of a nucleotide sequence of interest are disrupted differently but for which the disruptions overlap such that some genetic material has been removed from both alleles, and instances in which both alleles of the nucleotide sequence of interest share the same disruption. In various embodiments, disruptions of porcine CD37 and porcine CD81 may occur in at least one cell of the transgenic animal, at least a plurality of the animal's cells, at least half the animal's cells, at least a majority of animal's cells, at least a supermajority of the animal's cells, at least 70%, 75%, 80%, 85%, 90%, 95%, 98%, or 99% of the animal's cells.

The species of the mammal of this invention is not restricted, as far as it is non-human. Farm animals and experimental animals are examples. More particularly, such animals as the pig, bovine, equine, ovine, goat, dog, rabbit, mouse, rat, guinea pig, and hamster are examples. Although the application describes a typical non-human animal (pigs), other animals can similarly be genetically modified. As mentioned above, the pig is desirable in organ transplantation to humans. As used herein, the term "pig" refers to any pig known to the art including, but not limited to, a wild pig, domestic pig, mini pigs, a *Sus scrofa* pig, a *Sus scrofa domesticus* pig, as well as in-bred pigs. Without limitation the pig can be selected from the group comprising Landrace, Yorkshire, Hampshire, Duroc, Chinese Meishan, Chester White, Berkshire Goettingen, Landrace/York/Chester White, Yucatan, Bama Xiang Zhu, Wuzhishan, Xi Shuang Banna, and Pietrain pigs. Porcine organs, tissues or cells include organs, tissues, devitalized animal tissues, and cells from a pig.

Transgenic pigs as described herein can be achieved by, for example, altering, removing, or otherwise disrupting pCD37 alleles and/or pCD81 alleles, or replacement of pCD37 and/or pCD81 alleles with genetically modified sequences. In some cases, transgenic pigs are produced using homologous recombination and somatic cell nuclear transfer (SCNT) methods, such as those described in U.S. Pat. No. 7,989,675; US-2009-0241203-A1; Rogers et al., *Science* 321:1837-1841, 2008; Rogers et al., *J. Clin. Invest.* 118(4):1571-1577, 2008; Ostedgaard et al., *Sci. Transl. Med.* 3(74):74ra24, 2011, each of which is incorporated herein in its entirety by reference. Handmade cloning (HMC), originally described by Vajta et al. (*Cloning* 2001; 3:89-95) is based on SCNT but is a simpler technique for somatic cell cloning without the use of a micromanipulator. See also Vajta et al., *Trends Biotechnol.* 2007, 25(6):250-3.

Other methods for producing genetically modified non-human animals are generally known in the art, and are described in Sambrook et al, *Molecular Cloning, A Laboratory Manual*, Cold Spring Harbor Press, Cold Spring Harbor, N.Y. (1989), incorporated herein by reference. In some cases, genetic modifications are produced using a form of gene editing. The term "gene editing" and its grammatical equivalents as used herein refer to genetic engineering in which one or more nucleotides are inserted, replaced, or removed from a genome. For example, gene editing can be performed using a nuclease (e.g., a natural-existing nuclease or an artificially engineered nuclease). To date, several gene-knockout pigs have been generated using Zinc-finger nuclease (ZFN) and transcription activator-like effector nuclease (TALEN) gene-editing technologies.

In certain embodiments, Cas gene editing is performed using a CRISPR/Cas system (e.g., a type II CRISPR/Cas system). For example, a CRISPR/Cas system can be used to reduce expression of one or more genes in cells of a spheroid. In some cases, the protein expression of one or more endogenous genes is reduced using a CRISPR/Cas system. In other cases, a CRISPR/Cas system can be used to perform site specific insertion. For example, a nick on an insertion site in the genome can be made by CRISPR/Cas to facilitate the insertion of a transgene at the insertion site. Other methods of making genetic modifications suitable for use according to the methods provided herein include but are not limited to somatic cell nuclear transfer (SCNT) and introduction of a transgene. As used herein, the term "transgene" refers to a gene or genetic material that can be transferred into an organism or a cell thereof. Procedures for obtaining recombinant or genetically modified cells are generally known in the art, and are described in Sambrook et al, *Molecular Cloning, A Laboratory Manual*, Cold Spring Harbor Press, Cold Spring Harbor, N.Y. (1989), incorporated herein by reference.

In some cases, genetically modified pigs as described herein are produced by transfecting porcine cells with bicistronic sgRNA/Cas9-knockout vectors for pCD37 and pCD81 genes. The transfected cells exhibited biallelic gene silencing mutational events. When isolated, successfully mutated cells can be used to generate clonal animals by SCNT or another method. Genomic DNA of the resulting transgenic animals can be sequenced to confirm biallelic frameshift mutational events, indicating gene silencing at the targeted pCD37 and pCD81 loci. In some cases, such genetic editing steps can be performed using cells of a Gal-KO/CMAH-KO/B4GalNT2-KO triple knockout pig, thus generating a quintuple knockout lacking expression of functional non-Gal xenoantigens (e.g., pCD37 and pCD81) and Gal xenoantigens (e.g., αGal) as well as other non-Gal xenoantigens (e.g., Neu5Gc, and β4GalNT2).

In another aspect, provided herein are porcine organs, tissues, and cells obtained from genetically modified pigs described herein. In some cases, the porcine organs, tissues, and cells of a genetically modified pig are organs, tissues, and cells useful for transplantation including, without limitation, skin, a skin-related product, heart, liver, kidneys, lung, pancreas, thyroid, small bowel, and components thereof. As used herein, the term "skin related product" refers to products isolated from skin and products intended for use with skin. Skin related products isolated from skin or other tissues may be modified before use with skin. Skin related products include but are not limited to replacement dressings, burn coverings, dermal products, replacement dermis, dermal fibroblasts, collagen, chondroitin, connective tissue, keratinocytes, cell-free xenodermis, cell-free pig dermis, composite skin substitutes and epidermis and temporary wound coverings.

In another aspect, provided herein is transplant material encompasses organs, tissue and/or cells from an animal for use as xenografts. Transplant material for use, as xenografts, may be isolated from transgenic animals with decreased expression of pCD37 and/or pCD81, or from transgenic animals lacking pCD37 and/or pCD81. Transgenic transplant material from knockout pigs can be isolated from a prenatal, neonatal, immature or fully mature animal. The transplant material may be used as temporary or permanent organ replacement for a human subject in need of an organ transplant. Any porcine organ can be used including, but not limited to, the brain, heart, lungs, eye, stomach, pancreas, kidneys, liver, intestines, uterus, bladder, skin, hair, nails, ears, glands, nose, mouth, lips, spleen, gums, teeth, tongue, salivary glands, tonsils, pharynx, esophagus, large intestine, small intestine, small bowel, rectum, anus, thyroid gland, thymus gland, bones, cartilage, tendons, ligaments, suprarenal capsule, skeletal muscles, smooth muscles, blood vessels, blood, spinal cord, trachea, ureters, urethra, hypothalamus, pituitary, pylorus, adrenal glands, ovaries, oviducts, uterus, vagina, mammary glands, testes, seminal vesicles, penis, lymph, lymph nodes and lymph vessels.

To study the effects of various genetic modifications on human responses to porcine tissue transplants, it will be advantageous in some cases to generate transgenic pigs in which the genome has been genetically modified for reduced expression or to fully knock out expression of pCD37, pCD81, as well as other xenoreactive antigens or immune-related molecules. For example, genetically modified porcine cells (e.g., LSECs, hepatocytes, fibroblasts) can be genetically modified using a CRISPR/Cas system to selectively reduce expression of one or more major histocompatibility complex (MHC) molecules (e.g., MHC I molecules and/or MHC II molecules) as compared to a non-genetically modified counterpart animal. In some cases, porcine cells are engineered to genetically modify (e.g., mutate) or modulate (e.g., increase, decrease) the expression of genes such as pGGTA1, pCMAH, pB4GalNT2, human (h) CD46, hCD55, human thrombomodulin, CD46 (membrane co-factor protein), CD55 (decay-accelerating factor), CD59 (protectin or membrane inhibitor of reactive lysis), Human H-transferase (e.g., for expression of blood type 0 antigen), Endo-β-galactosidase C (e.g., for reduction of Gal antigen expression), α1,3-galactosyltransferase, Cytidine monophosphate-N-acetylneuraminic acid hydroxylase (CMAH), β1,4-N-acetylgalactosaminyltransferase (β4GalNT2) (e.g., β4GalNT2 knock out), CIITA-DN (e.g., MHC class II transactivator knockdown, resulting in swine leukocyte antigen class II knockdown), Class I WIC-knockout (WIC-TKO), HLA-E/human β2-microglobulin (e.g., to inhibit human natural killer cell cytotoxicity), Human FAS ligand (CD95L), Human N-acetylglucosaminyltransferase III (GnT-III) gene, Porcine CTLA4-Ig (cytotoxic T lymphocyte antigen 4 or CD152), Human TRAIL (tumor necrosis factor-α-related apoptosis-inducing ligand), von Willebrand factor (vWF), Human tissue factor pathway inhibitor (TFPI), Human endothelial protein C receptor (EPCR), Human ectonucleoside triphosphate diphosphohydrolase-1 (CD39), Human tumor necrosis factor-α-induced protein 3 (A20), Human haem oxygenase-1 (HO-1), Human CD47 (species-specific interaction with SIRP-α inhibits phagocytosis), Porcine asialoglycoprotein receptor 1 (ASGR1) (e.g., to decrease platelet phagocytosis), Human signal regulatory protein-α (SIRPα) (e.g., to decrease platelet, phagocytosis by 'self' recognition), human IL-6R (e.g., to reduce inflammation), human leukocyte antigen G (HLA-G) (e.g. 'to induce tolerance).

As used herein, the terms "synthetic" and "engineered" are used interchangeably and refer to a non-naturally occurring material that has been created or modified by the hand of man (e.g., a genetically modified animal having one or predetermined engineered genetic modifications in its genome) or is derived using such material (e.g., a tissue or organ obtained from such genetically modified animal). In some cases, cells used to produce transgenic animals of this disclosure are porcine cells that contain one or more synthetic or genetically engineered nucleic acids (e.g., a nucleic acid containing at least one artificially created insertion, deletion, inversion, or substitution relative to the sequence found in its naturally occurring counterpart). Cells comprising one or more synthetic or engineered nucleic acids are considered to be engineered or genetically modified cells. As used herein, the term "engineered tissue" refers to aggregates of engineered/genetically modified cells.

Expression of a gene product is decreased when total expression of the gene product is decreased, a gene product of an altered size is produced, or when the gene product exhibits an altered functionality. Thus, if a gene expresses a wild-type amount of product but the product has an altered enzymatic activity, altered size, altered cellular localization pattern, altered receptor-ligand binding or other altered activity, expression of that gene product is considered decreased. Expression may be analyzed by any means known in the art including, but not limited to, RT-PCR, Western blots, Northern blots, microarray analysis, immunoprecipitation, radiological assays, polypeptide purification, spectrophotometric analysis, Coomassie staining of acrylamide gels, ELISAs, 2-D gel electrophoresis, in situ hybridization, chemiluminescence, silver staining, enzymatic assays, ponceau S staining, multiplex RT-PCR, immunohistochemical assays, radioimmunoassay, colorimetric analysis, immunoradiometric assays, positron emission tomography, fluorometric assays, fluorescence activated cell sorter staining of permeabilized cells, radioimmunosorbent assays, real-time PCR, hybridization assays, sandwich immunoassays, flow cytometry, SAGE, differential amplification, or electronic analysis. See, for example, Ausubel et al, eds. (2002) Current Protocols in Molecular Biology, Wiley-Interscience, New York, New York; Coligan et al (2002) Current Protocols in Protein Science, Wiley-Interscience, New York, New York; herein incorporated by reference in their entirety.

Expression may be analyzed directly or indirectly. Indirect expression analysis may include but is not limited to, analyzing levels of a product catalyzed by an enzyme to evaluate expression of the enzyme. See for example, Ausubel et al, eds (2013) Current Protocols in Molecular Biology, Wiley-Interscience, New York, N.Y. and Coligan et al (2013) Current Protocols in Protein Science, Wiley-Interscience New York, N.Y.

As used herein, "as compared to" is intended encompass comparing something to a similar but different thing, such as comparing a data point obtained from an experiment with a knockout pig to a data point obtained from a similar experiment with a wild-type pig. The word "comparing" is intended to encompass examining the character, qualities, values, quantities or ratios in order to discover resemblances or differences between that which is being compared. Comparing may reveal a significant difference in that which is being compared. By "significant difference" is intended a statistically significant difference in results obtained for multiple groups, such as the results for a first aliquot and a second aliquot. Generally, statistically significance is assessed by a statistical significance test such as but not limited to the student's t-test, Chi-square, one-tailed t-test, two-tailed t-test, ANOVA, Dunett's post hoc test, Fisher's test and z-test. A significant difference between the two results may be results with a $p<0.1$, $p<0.05$, $p<0.04$, $p<0.03$, $p<0.02$, or $p<0.01$ or greater.

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Nucleic acids can be obtained using any suitable method, including those described by Maniatis et al., Molecular Cloning: A Laboratory Manual, Cold Spring Harbor, N.Y., pp. 280-281 (1982). In some aspects, nucleic acids are obtained as described in U.S. Patent Application Publication No. US2002/0190663. Nucleic acids obtained from biological samples typically are fragmented to produce suitable fragments for analysis.

Nucleic acids and/or other moieties of the invention may be isolated. As used herein, "isolated" means separate from at least some of the components with which it is usually associated whether it is derived from a naturally occurring source or made synthetically, in whole or in part. Nucleic acids and/or other moieties of the invention may be purified. As used herein, "purified" means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

In another aspect, provided herein is a method of improving a rejection related symptom in a human subject. In some cases, the method comprises transplanting porcine transplant material having reduced levels of pCD37 antigens and reduced levels of pCD81 antigens into a human subject in need thereof wherein a rejection related symptom is improved as compared to when porcine transplant material from a wild-type pig is transplanted into a human subject. Transplant rejection occurs when transplanted tissue, organs, cells or other biological material are not accepted by the recipient's body. In transplant rejection, the recipient's immune system attacks the transplanted material. Multiple types of transplant rejection exist and may occur separately or together. Rejection processes included but are not limited to hyperacute rejection (HAR), acute humoral xenograft rejection reaction (AHXR), thrombocytopenia, acute humoral rejection, hyperacute vascular rejection, antibody mediated rejection and graft versus host disease. By "hyperacute rejection" we mean rejection of the transplanted material or tissue occurring or beginning within the first 24 hours post-transplant involving one or more mechanisms of rejection. Rejection encompasses but is not limited to "hyperacute rejection," "humoral rejection," "acute humoral rejection," "cellular rejection," and "antibody mediated rejection." Acute humoral xenograft reaction (AHXR) is characterized by a spectrum of pathologies including without limitation acute antibody mediated rejection occurring within days of transplant, the development of thrombotic microangiopathy (TMA), microvascular angiopathy, pre-formed non-Gal IgM and IgG binding, complement activation, microvascular thrombosis and consumptive thrombocytopenia within the first few weeks post-transplant.

In certain embodiments, xenotransplantation of a porcine organ, tissue, or cell from a transgenic pig described herein results in an improvement of one or more rejection related symptoms selected from a cellular rejection response related symptom, a humoral rejection response related symptom, a hyperacute rejection (HAR) related symptom, an acute humoral xenograft reaction rejection related symptom, and an acute vascular rejection response related symptom wherein one or more rejection related symptoms is improved as compared to when tissue from a wild-type swine is transplanted into a human. By "improving," "bettering," "ameliorating," "enhancing," and "helping" is intended advancing or making progress in what is desirable. It is also envisioned that improving a rejection related symptom may encompass a decrease, lessening, or diminishing of an undesirable symptom. It is further recognized that a rejection related symptom may be improved while another rejection related symptom is altered.

In interpreting this disclosure, all terms should be interpreted in the broadest possible manner consistent with the context. It is understood that certain adaptations of the invention described in this disclosure are a matter of routine optimization for those skilled in the art, and can be implemented without departing from the spirit of the invention, or the scope of the appended claims.

So that the compositions and methods provided herein may more readily be understood, certain terms are defined:

Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements.

The terms "about" and "approximately" shall generally mean an acceptable degree of error for the quantity measured given the nature or precision of the measurements. Typical, exemplary degrees of error are within 10%, and preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Various exemplary embodiments of compositions and methods according to this invention are now described in the following non-limiting Examples. The Examples are offered for illustrative purposes only and are not intended to limit the scope of the present invention in any way. Indeed, various modifications in addition to those shown and described herein will become apparent to those skilled in the art from the foregoing description and the following examples and fall within the scope of the appended claims.

EXAMPLES

Example 1—Porcine Xenoreactive NonGal Antigens

Methods

Full-length pCD37 and pCD81 cDNAs were synthesized based on the corresponding DNA sequences in NCBI GenBank based on all available isoforms.

Amplification of the CD37 gene: Using 1% DMSO treatment in accordance with the PWO Superyield DNA Polymerase kit, PCR was run with a 2 minute period of denaturation at 94° C., followed by 40 cycles of 15 seconds of denaturing at 94° C., 30 seconds of annealing at 60.6° C., and 50 seconds of elongation at 72° C. A fifth step of 7 minutes elongation at 72° C. followed the 40 cycles, and the thermocycler kept the PCR product at 16° C. upon completion. Porcine splenocyte cDNA and two different primers were used. The first consisted of a pure X5 isoform mix, with the forward having the sequence 5'-ATG GGC CTT GCC CTC CTG G-3' (SEQ ID NO:1), and the reverse having the sequence 5'-CTA GCG GTA CCG AGC CCG-3' (SEQ ID NO:2), which would yield a 643 bp band after electrophoresis. The second primer used the reverse X5 isoform primer and the forward X2 isoform primer, with the sequence 5'-ATG TCG GCC CAG GCC AGC-3' (SEQ ID NO:3), and the mix would yield a 848 bp band after agarose gel electrophoresis. Once the bands were obtained, a QIAquick® Gel Extraction Kit (250) was used to purify the PCR product in the bands. Once purified, the samples were sent into Genwiz, in accordance with their submission guidelines, for sequencing.

Cloning and Transforming Bacteria: The Zeroblunt® TOPO PCR Cloning Kit for Sequencing was used to clone the purified PCR product, with the Zeroblunt TOPO vector being used in accordance with their protocol. Once the reaction had finished, it was transferred to a tube of chemically competent E. coli, where the bacteria endured heat shock to induce transformation of the colony. After recovering, the transformed bacteria were spread on ampicillin-treated plates in 2 different concentrations; while 50 µL was taken to spread onto one plate, the remaining mixture was spun down to create a cell pellet, and 150 µL of supernatant was removed to create 50 µL of more concentrated solution to be spread on the second plate. The plates were left to incubate overnight at 37° C.

Culturing Transformed Bacteria: A 300 µL pipette tip was used to scrape some of a bacterial colony off of a plate, to mix it in a conical tube of 3 mL SOC/Amp+ media. This was done for each plate, and the tubes were left to shake at 250 rpm and 37° C. for 7 hours.

Sequencing: The bacterial cultures were lysed and the plasmid loops were extracted using the QIAprep® Spin Miniprep Kit, with 30 µL of EB used to elute the plasmid loops from the spin column membrane. The samples were sent into Genwiz sequencing in accordance with their submission guidelines.

FLAG-tag was added to the C-terminus of pCD37 and pCD81, respectively. pCD37 and pCD81 cDNA were cloned into an expression vector with a CMV promoter. Human HEK293 T cells were transfected with pCD37/pCD81 cDNA, and human IgG/IgM binding was determined by flow cytometry. Furthermore, porcine wildtype fetal fibroblasts (WT-FF) and porcine GalKO fetal fibroblasts (GalKO-FF) were transfected with pCD37 and pCD81 cDNA for overexpression, and human IgG binding was evaluated by flow cytometry using 3 different human serum samples.

Results

Figure 1:
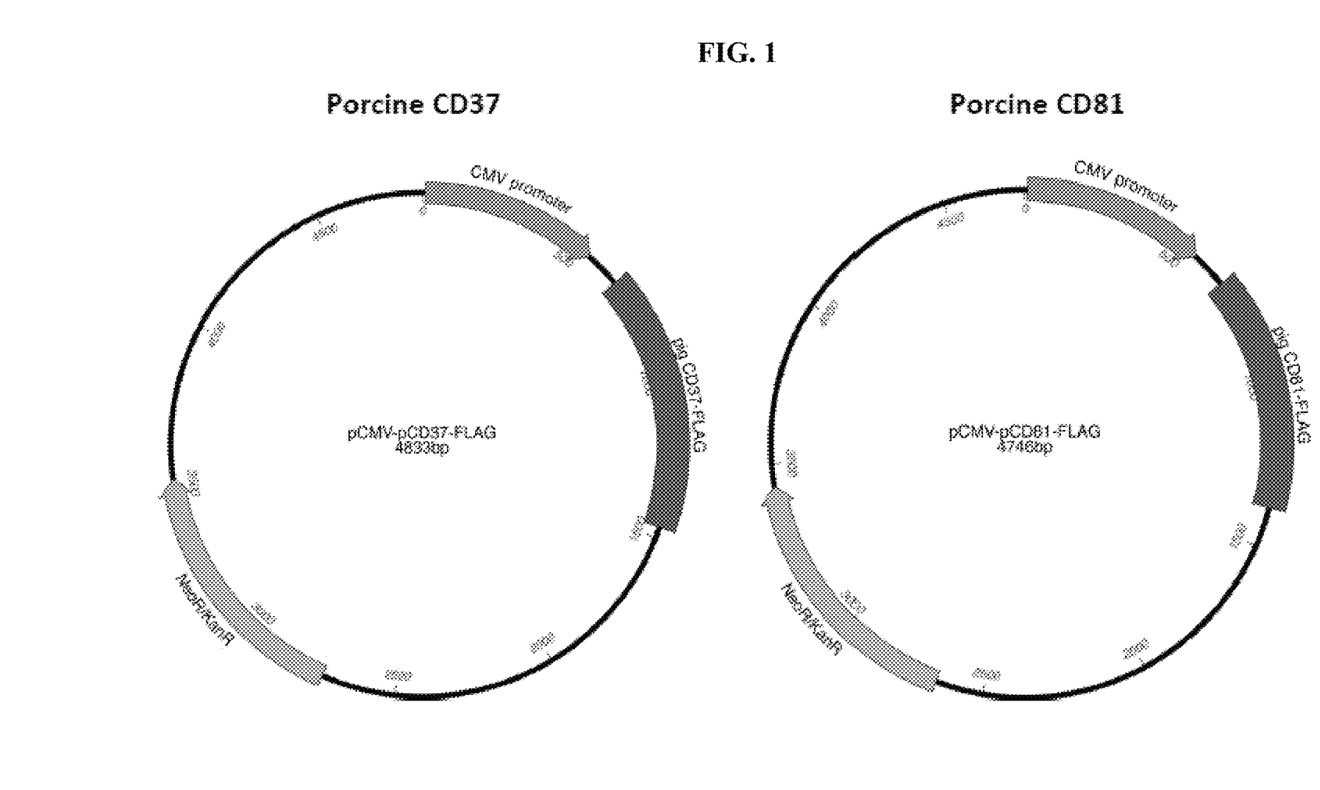
FIG. 1 presents porcine (p) pCD37 and pCD81. CMV promoter is used to create a vector for pCD37 and pCD81.
Figure 2:
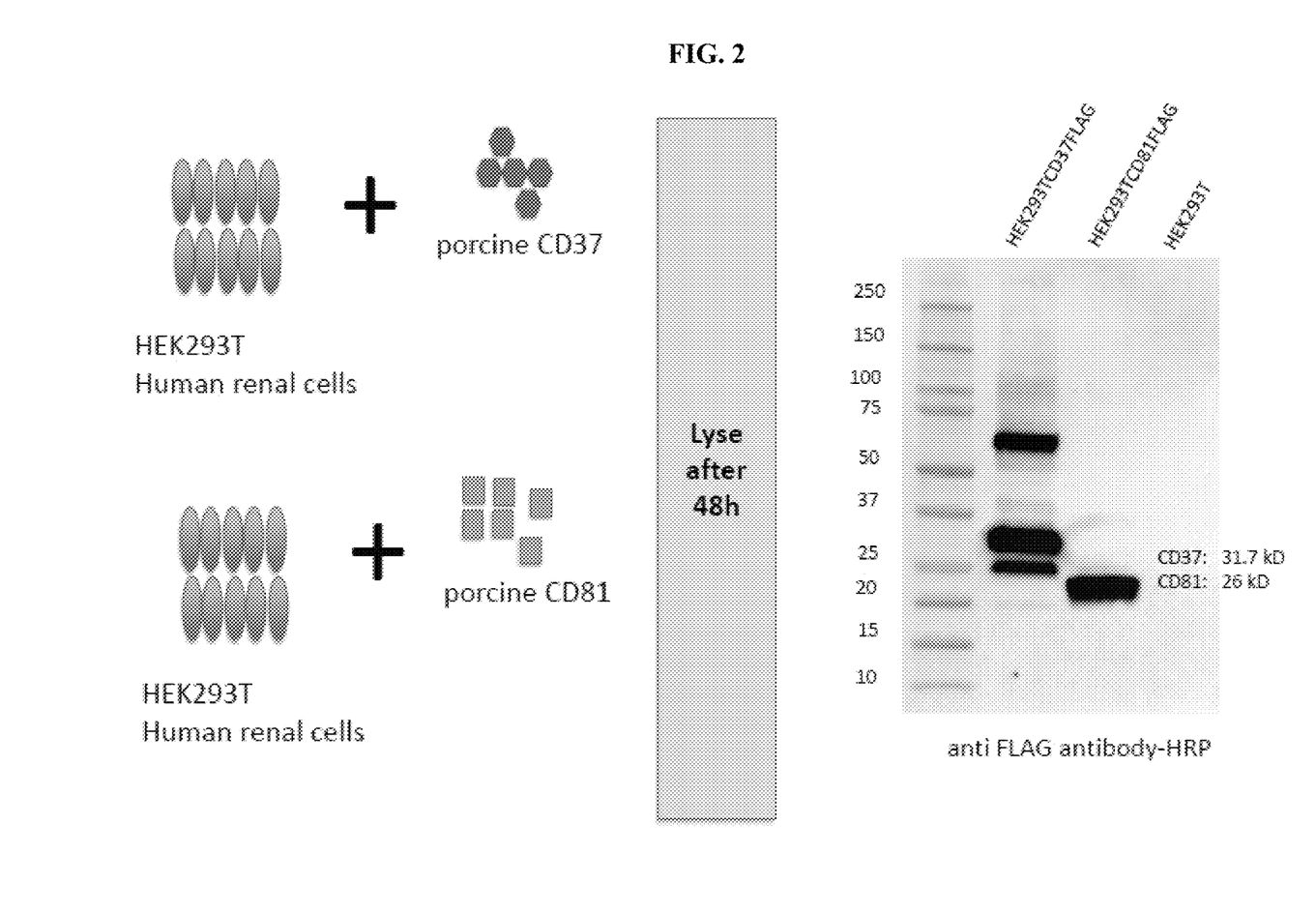
FIG. 2 demonstrates exogenous expression in HEK293T cells transfected with pCD37 and pCD81. Transfected cells were lysed after 48 hours. Western blot shows pCD37 and pCD81 expression on those cells.
Figure 3:
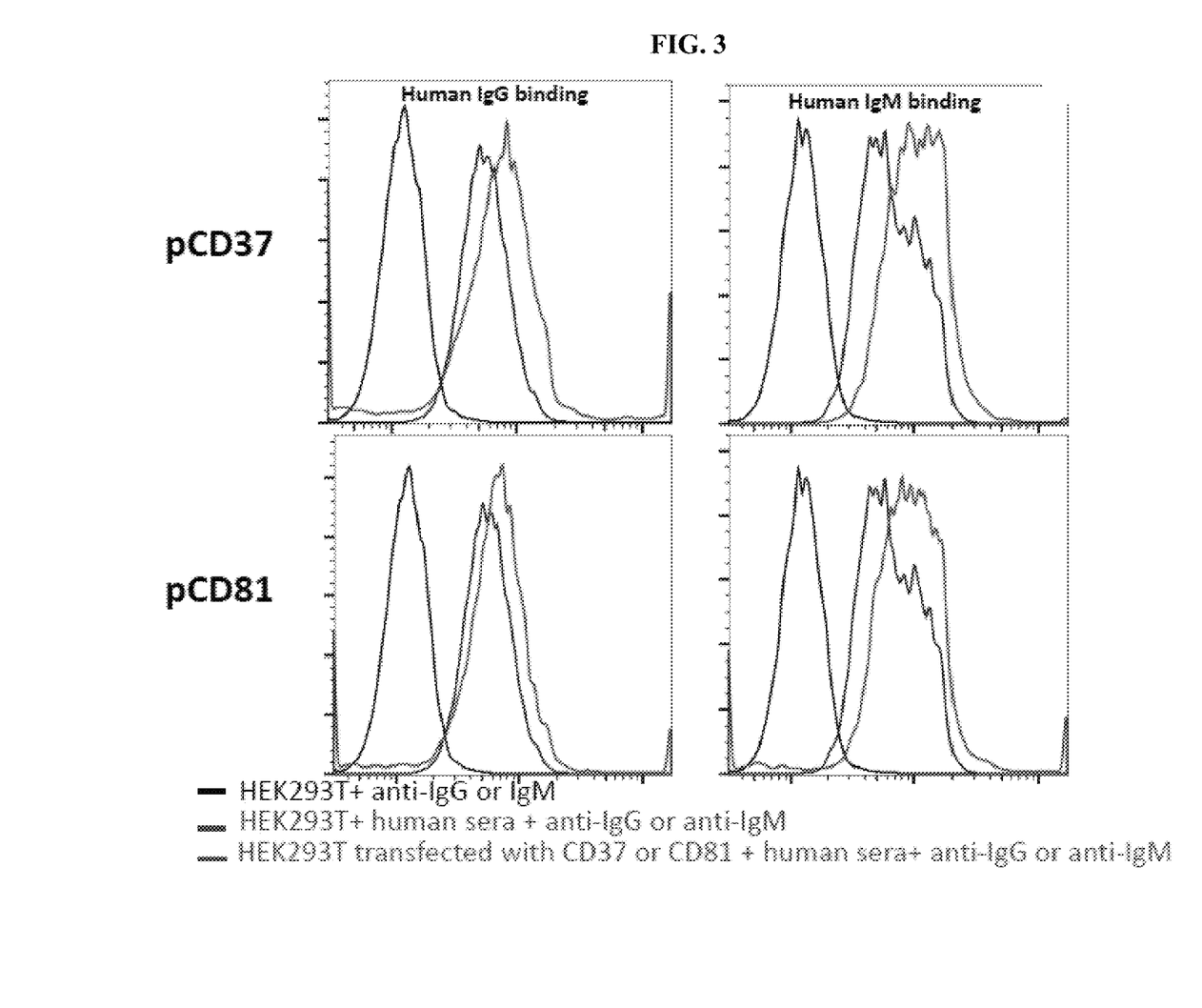
FIG. 3 demonstrates human IgG/IgM binding with pCD37 and pCD81 on HEK293T cells.
Figure 4:
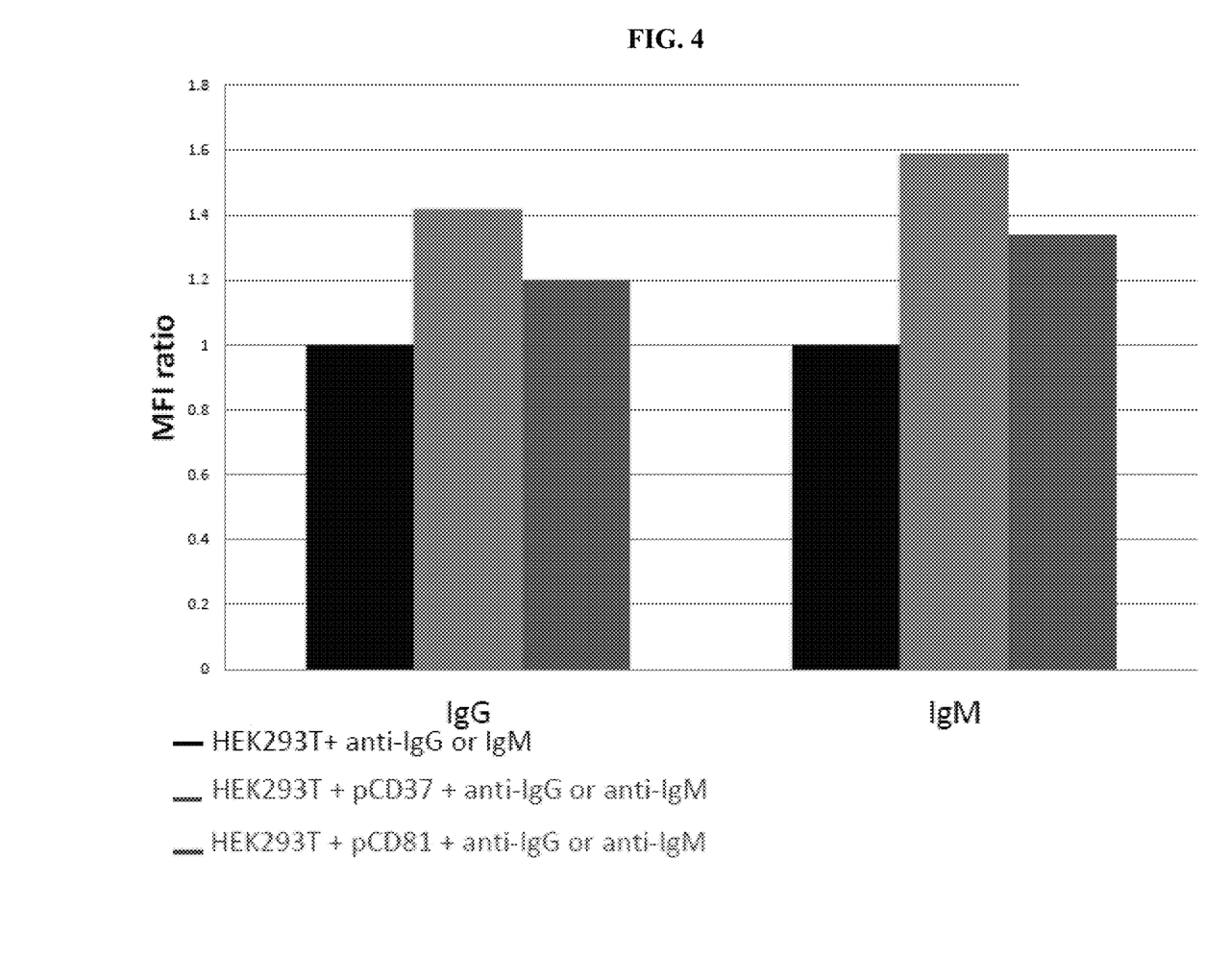
FIG. 4 presents the mean fluorescence intensity (MFI) ratio of human IgG/IgM binding with pCD37 and pCD81 on the HEK293T cells of FIG. 3.
Figure 5:
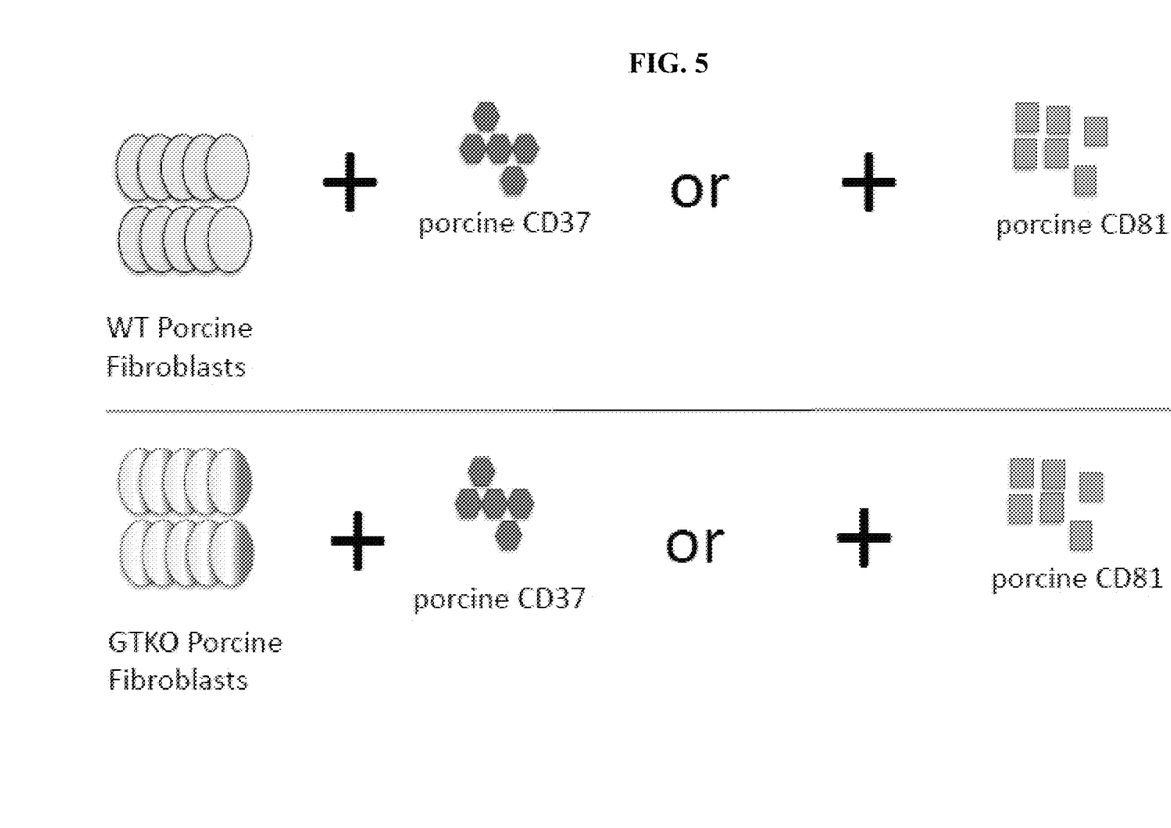
FIG. 5 demonstrates wild-type or Gal-knockout (GalKO) porcine fibroblast overexpression of pCD37 and pCD81.
Figure 6:
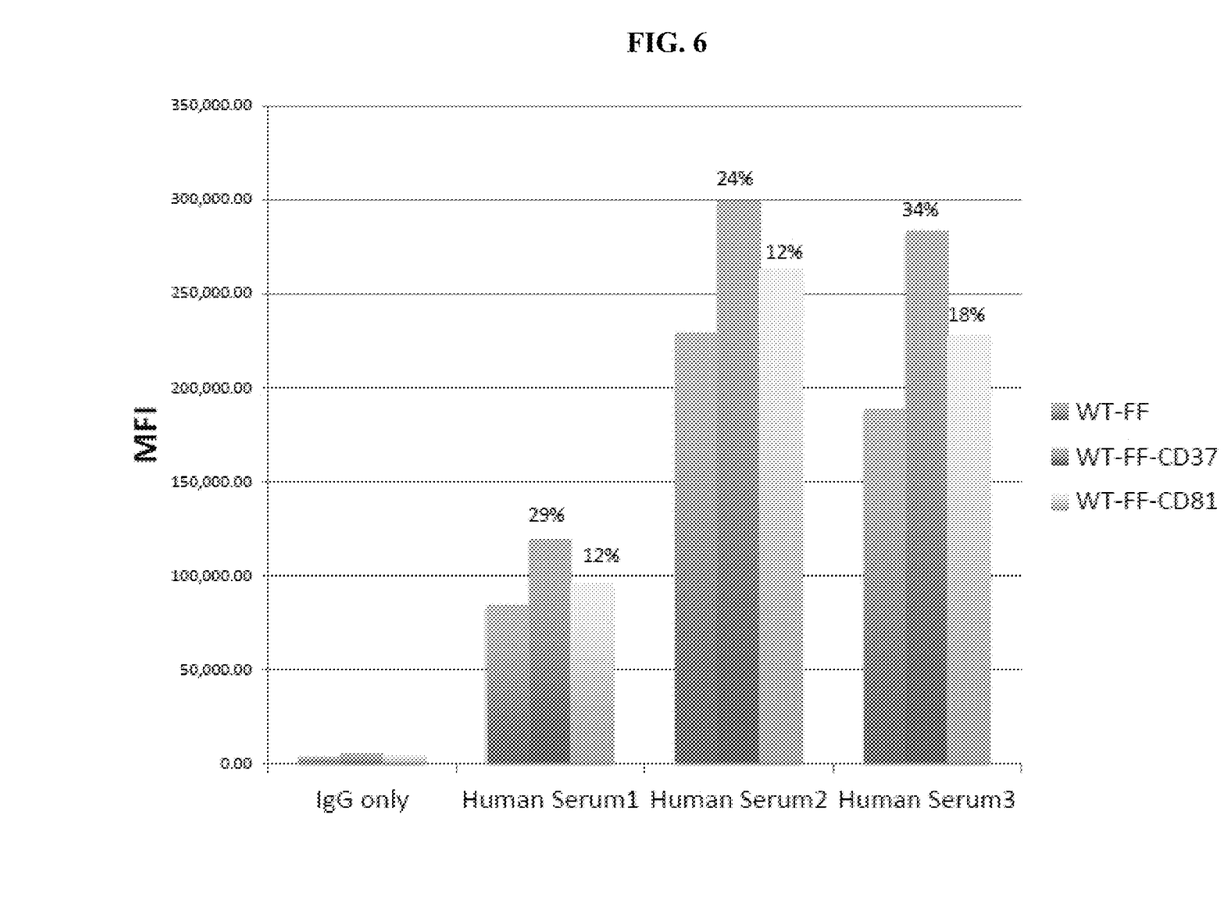
FIG. 6 demonstrates human IgG binding to wildtype porcine fibroblasts overexpressing pCD37 and pCD81.
Figure 7:
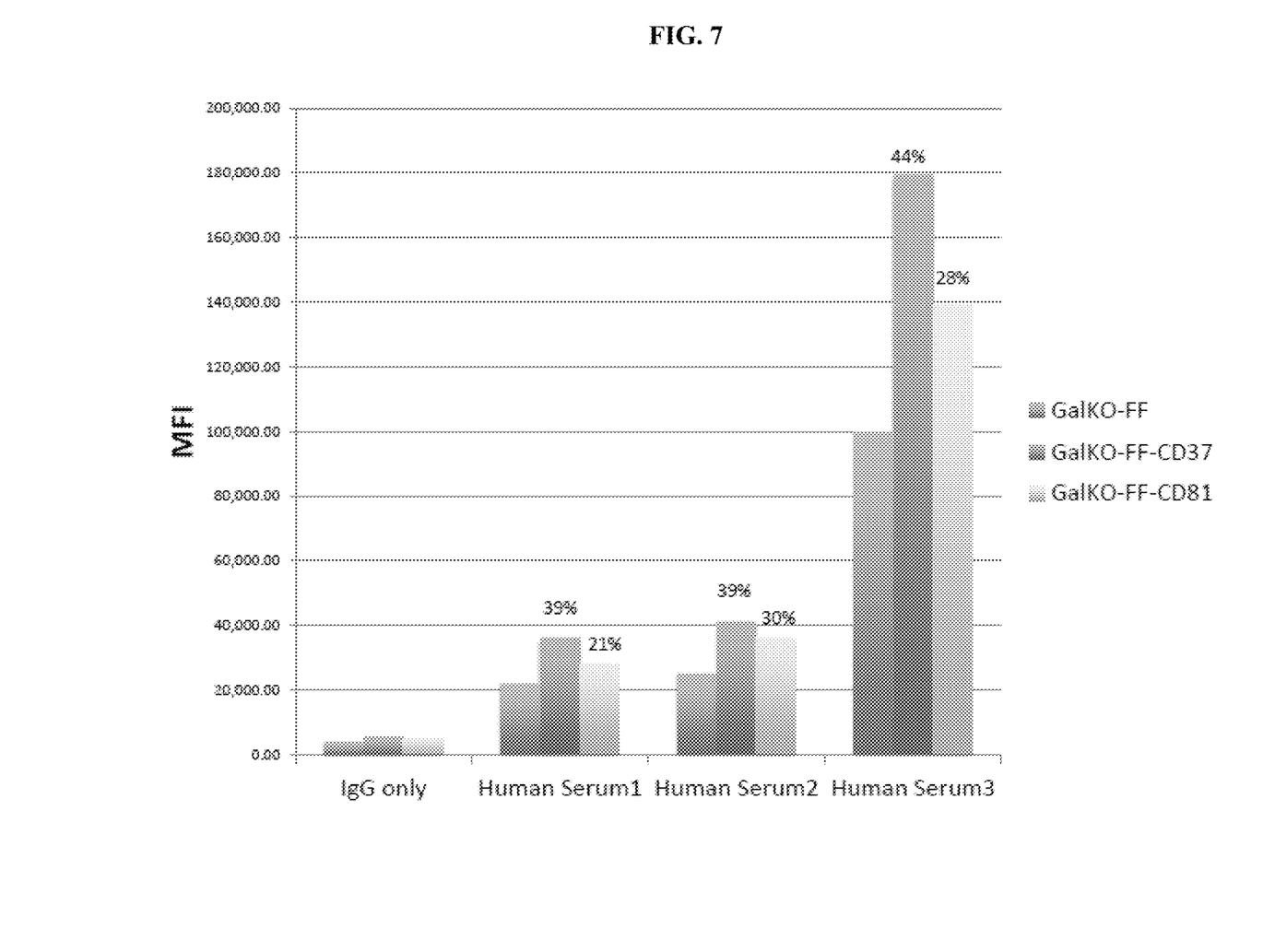
FIG. 7 demonstrates human IgG binding to GalKO porcine fibroblasts overexpressing pCD37 and pCD81.

Expression of pCD37 and pCD81 in human HEK293T cells was confirmed using anti-FLAG antibody by western blotting (FIG. 2). pCD37 and pCD81 cDNA-transfected HEK293T cells exhibited 40% and 20% more human IgG binding, and 60% and 35% more human IgM binding, respectively, as compared to control HEK293T cells only (FIG. 4). Similar results were observed in both wildtype fetal fibroblasts (WT-FF) and porcine GalKO fetal fibroblasts (GalKO-FF) after transfection of pCD37 and pCD81 cDNA. WT-FF-pCD37 and WT-FF-pCD81 cells showed an average of 30% and 14% more human IgG binding, respectively, compared to WT-FF cells only (FIG. 6). By using GalKO-FF cells to lower the high background binding to WT cells, human IgG binding was significantly reduced, as measured by mean fluorescence intensity (MFI) (FIG. 7). Despite overall low IgG binding, as expected, human IgG binding to GalKO-FF-pCD37 and GalKO-FF-pCD81 was increased by an average of 41% and 26%, respectively, compared to GalKO-FF cells only.

Figure 8:
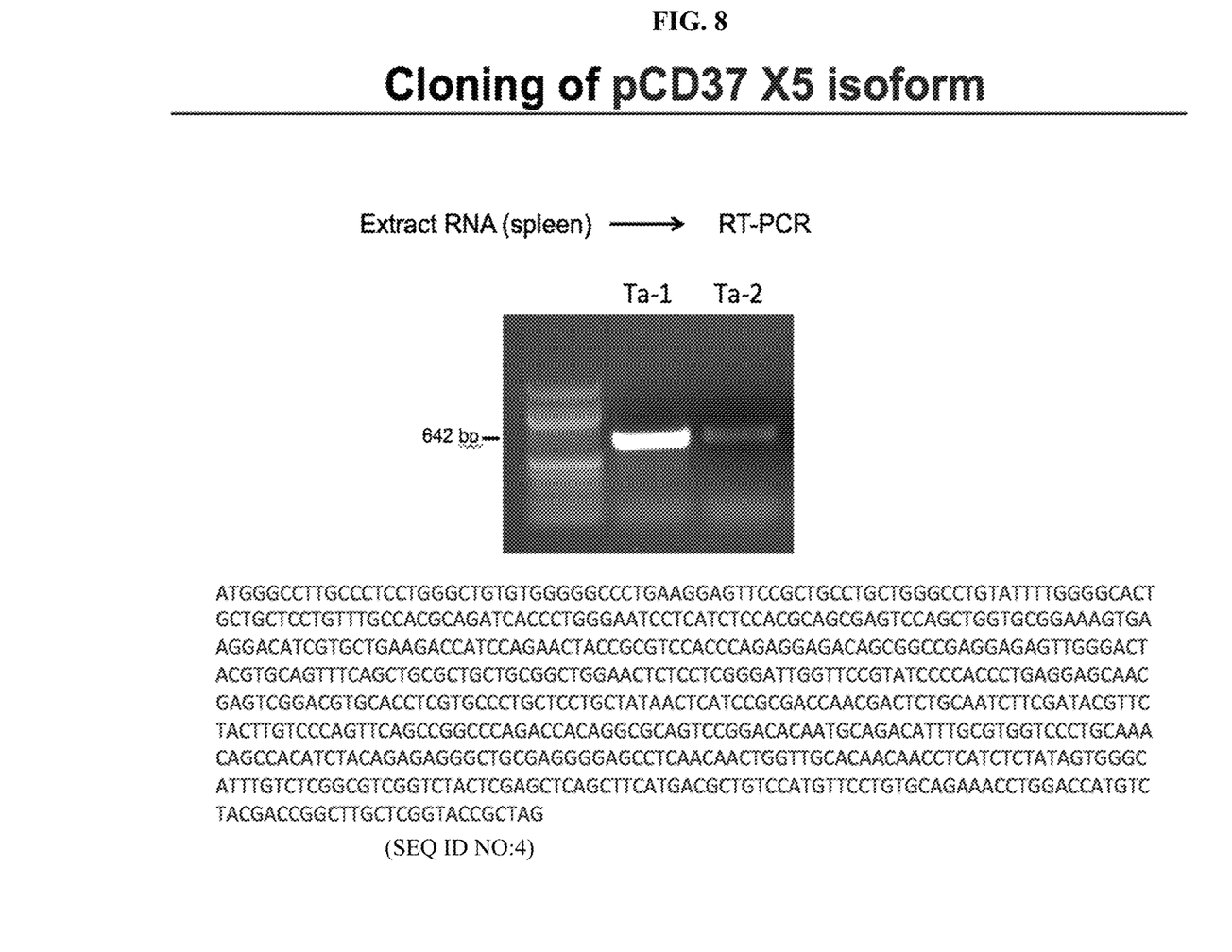
FIG. 8 demonstrates an isoform of porcine CD37 sequence.

After the confirmation of pCD37 and pCD81 as novel xenoreactive nonGal antigens, different isoforms of pCD37 gene were cloned. An example is shown in FIG. 8.

Figure 9:
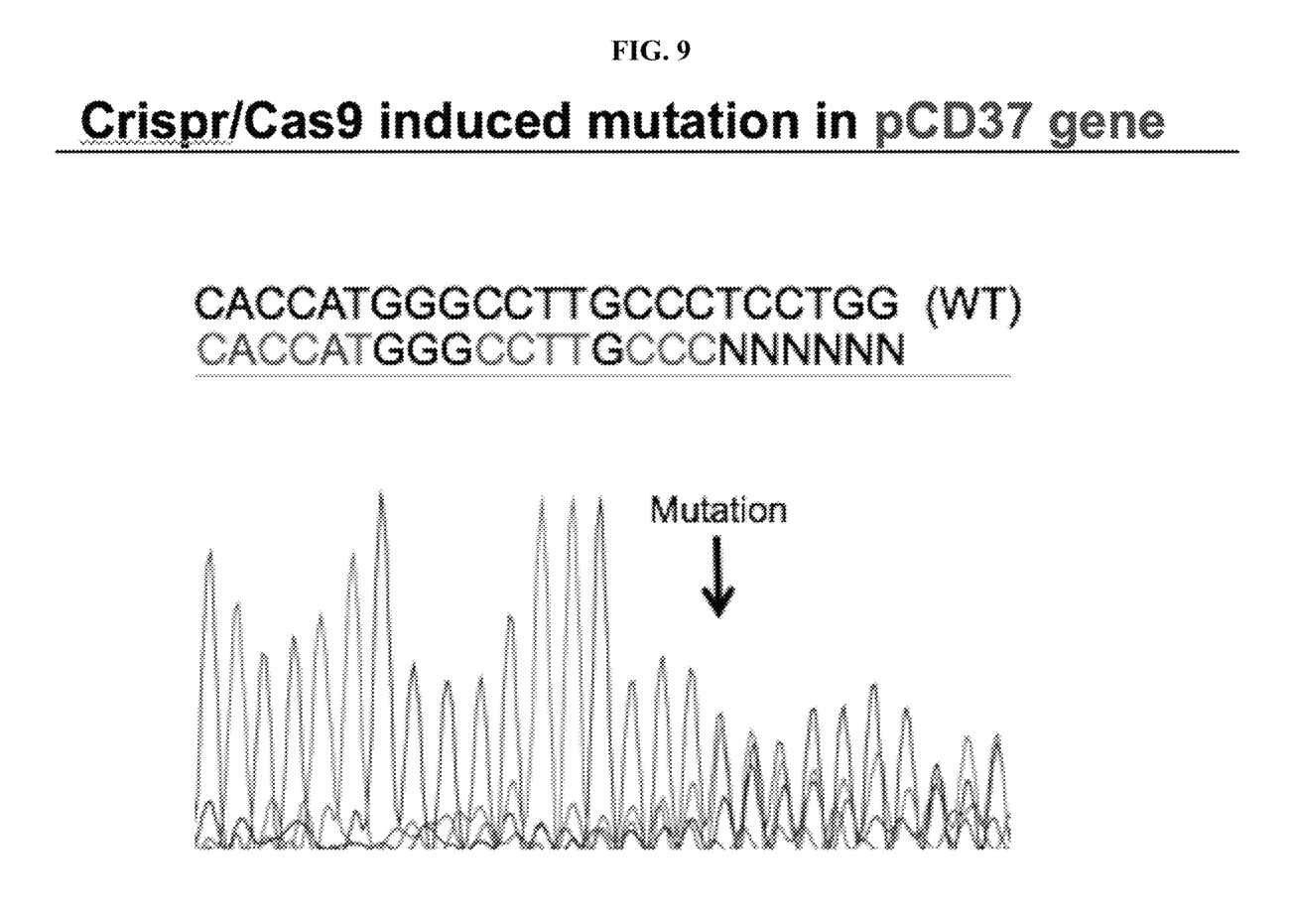
FIG. 9 demonstrates a CRISPR/Cas9 induced mutation in pCD37 gene.

Using CRISPR/Cas technology, a mutation of pCD37 gene in a pig genome has been created (FIG. 9).

Figure 10:
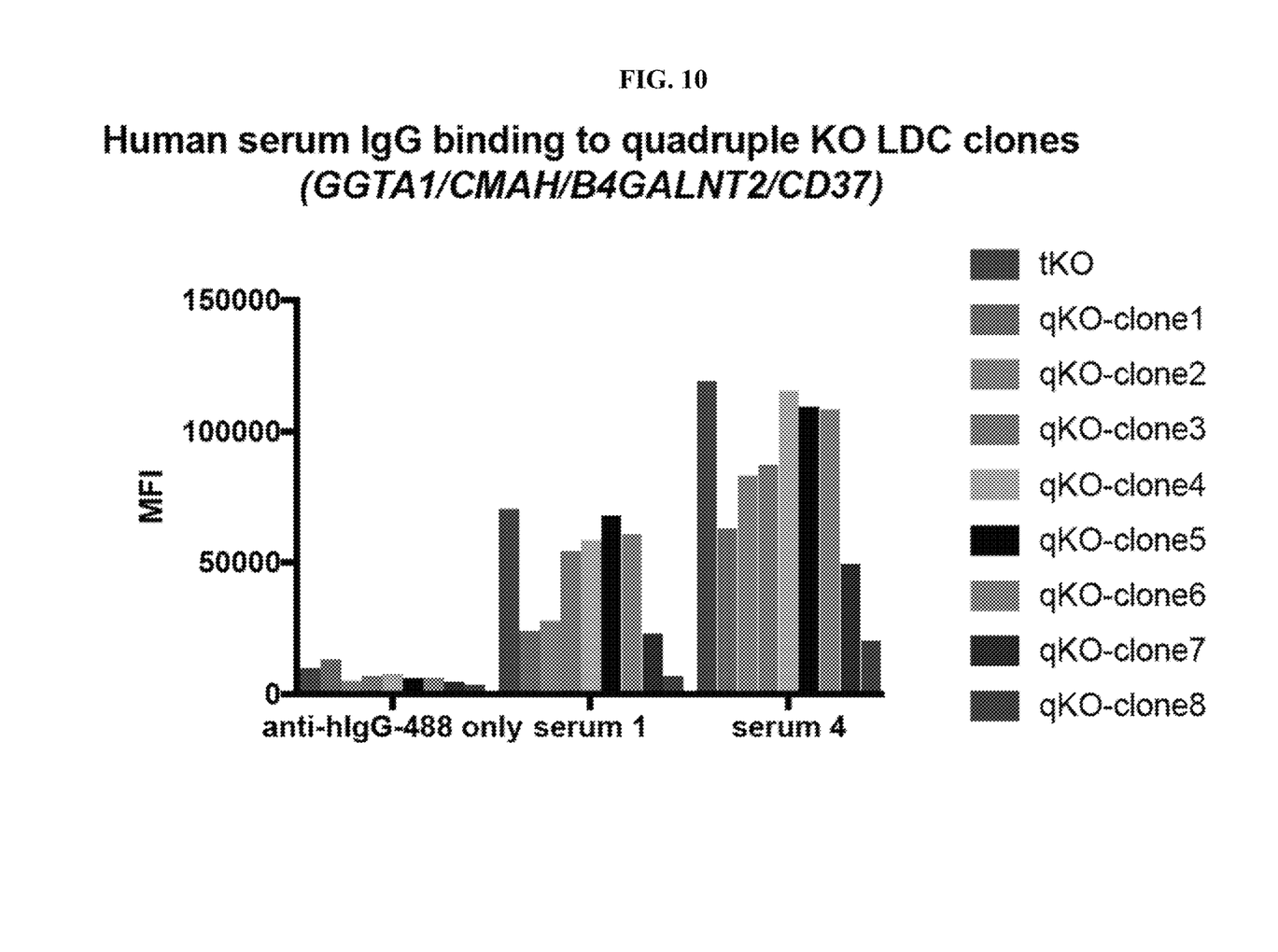
FIG. 10 demonstrates human IgG binding to quadruple knockout (GGTA1/CMAH/B4GALNT2/CD37) liver derived cells (LDC).

Quadruple gene-knockout porcine cell line was created on Gal-KO/CMAH-KO/B4GalNT2-KO background knocking out pCD37. Several different clones of quadruple gene-knockout (Gal-KO/CMAH-KO/B4GalNT2-KO/pCD37-KO) have been generated and tested for human IgG binding using 100% PRA human sera (FIG. 10).

Discussion

We identified for the first time in the literature that porcine (p) tetraspanins pCD37 and pCD81 are xenoreactive nonGal antigens. Increased human antibody binding to pCD37- and pCD81-transfected human HEK293T cells and porcine FF (WT and GalKO) demonstrated that tetraspanins pCD37 and pCD81 are novel xenoreactive antigens. We also created for the first time in the literature quadruple gene-knockout porcine cell line (Gal-KO/CMAH-KO/B4GalNT2-KO/pCD37-KO) performing pCD37 gene knockout from the pig genome. The data also suggest that pCD37 and pCD81 are important for reducing human immunoglobulin binding to GalKO cells relative to WT pig cells.

We claim:

1. A genetically modified porcine cell, wherein the genetic modifications comprise modifications to the genome of the porcine cell that results in the lack of any expression of functional pCD37 (pCD37KO), wherein said genetically modified porcine cell exhibits reduced binding to human immunoglobulins IgG and IgM relative to a porcine cell lacking said genetic modifications.

2. The genetically modified porcine cell of claim 1, further comprising modifications to the genome of the porcine cell that result in lack of any expression of functional α(1,3)-galactosyltransferase (αGT), cytidine monophosphate-N-acetylneuraminic acid hydroxylase (CMAH), and β1,4 N-acetylgalactosaminyl transferase (B4GalNT2) relative to a porcine cell lacking said modifications to the genome, wherein the modified porcine cell exhibits an absence of αGal antigens, a reduced level of N-Glycolylneuraminic acid (Neu5Gc) antigens, and a reduced level of B4GalNT2 antigens as compared to a porcine cells lacking said genetic modifications.

3. The cell of claim 1, wherein the genetic modification comprises a modification to the CD37 gene.

4. The cell of claim 1, further comprising a genetic modification that results in the lack of expression of functional pCD81.

5. The cell of claim 4, wherein the genetic modification comprises a modification of the CD81 gene.

* * * * *